United States Patent
Kobilka et al.

(10) Patent No.: US 10,832,800 B2
(45) Date of Patent: Nov. 10, 2020

(54) SYNTHETIC PATHWAY ENGINE

(71) Applicant: International Business Machines Corporation, Armonk, NY (US)

(72) Inventors: Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 483 days.

(21) Appl. No.: 15/397,167

(22) Filed: Jan. 3, 2017

(65) Prior Publication Data

US 2018/0189445 A1    Jul. 5, 2018

(51) Int. Cl.
| | |
|---|---|
| G05B 21/00 | (2006.01) |
| G16B 50/00 | (2019.01) |
| G16B 5/00 | (2019.01) |
| G16B 45/00 | (2019.01) |

(52) U.S. Cl.
CPC .............. *G16B 50/00* (2019.02); *G16B 5/00* (2019.02); *G16B 45/00* (2019.02)

(58) Field of Classification Search
CPC ....................... G05D 21/00; B01J 2219/00211
USPC ................................................. 700/268, 266
See application file for complete search history.

(56) References Cited

U.S. PATENT DOCUMENTS

| | | | |
|---|---|---|---|
| 5,862,514 A | 1/1999 | Huse et al. | |
| 5,981,733 A | 11/1999 | Gamble et al. | |
| 6,434,490 B1 | 8/2002 | Agrafiotis et al. | |
| 6,571,226 B1 | 5/2003 | Mydlowec et al. | |
| 7,188,055 B2 | 3/2007 | Agrofiotis et al. | |
| 7,250,950 B2 | 7/2007 | Smith et al. | |
| 2004/0003000 A1* | 1/2004 | Smith | G16C 20/10 |
| 2014/0188566 A1 | 7/2014 | Pinel et al. | |
| 2015/0133306 A1* | 5/2015 | Cronin | B01J 19/0046 |
| | | | 506/1 |

FOREIGN PATENT DOCUMENTS

| | | |
|---|---|---|
| WO | WO-2007/059403 A2 | 5/2007 |
| WO | WO-2011/049312 A2 | 4/2011 |

OTHER PUBLICATIONS

Wiley, ChemPlanner, ChemPlanner.com (online), accessed Feb. 15, 2017, 2 pages, URL: www.chemplanner.com.
IBM, *IBM BAO strategic IP insight platform (SIIP)*, IBM.com (online), accessed Feb. 15, 2017, 1 page, URL: www-935.ibm.com/services/us/gbs/bao/siip/.

(Continued)

*Primary Examiner* — Natalia Levkovich
(74) *Attorney, Agent, or Firm* — Peter K. Suchecki

(57) ABSTRACT

A process includes receiving information associated with a target molecule to be synthesized via a synthetic pathway engine user interface. The process also includes determining, using a synthetic pathway engine, synthetic pathway data for synthesis of the target molecule. In some cases, the process further includes generating a synthetic pathway report user interface that includes information associated with the synthetic pathway data. In other cases, the process further includes initiating automated synthesis of the target molecule using automated chemical synthesis equipment according to the synthetic pathway data.

20 Claims, 8 Drawing Sheets

(56) References Cited

OTHER PUBLICATIONS

Youtube, *Discover game-changing intellectual property insights delivered on the cloud*, video, uploaded Oct. 10, 2011, 16 pages, youtube.com (online), URL: www.youtube.com/watch?v=0-C1ZEBK4ig&cm_mc_uid=89510224733514854607708&cm_mc_sid_50200000=1485460770.
Bioscreening, "First auto carbohydrate synthesiser", BioScreening.net (online), Mar. 2009, 2 pages, URL: www.bioscreening.net/2009/03/24/first-auto-carbohydrate-synthesiser/.
Sanderson, "Complex molecules made to order in synthesis machine", Nature.com (online), Mar. 2015, 2 pages, URL: www.nature.com/news/complex-molecules-made-to-order-in-synthesis-machine-1.17113.
Drug Discovery & Development, "Automated Synthesizer", Product Release, Drug Discovery & Development Magazine, (DDDMag.com; online), Jun. 2010, 2 pages, URL: www.dddmag.com/product-release/2010/07/automated-synthesizer.
Sigma-Aldrich, "Substructure Search", SigmaAldrich.com (online), accessed Sep. 22, 2016, 2 pages, URL: http://www.sigmaaldrich.com/catalog/search/substructure/SubstructureSearchPage.

\* cited by examiner

SYNTHETIC PATHWAY ENGINE

BACKGROUND

A tedious and time-consuming aspect of research and development of new materials is the synthesis and characterization of new molecules and reaction pathways. The research process can be divided into three main phases. The first phase includes background research and planning of a synthetic pathway to a target material. The planning phase involves the careful consideration of a number of different factors. Examples of such factors include cost and availability of reagents, toxicity of reagents, time required to complete reactions and purification, overall yield of subsequent reactions, and the availability of appropriate laboratory equipment. While chemical reaction and literature searching software exists, significant personnel hours are still required to screen through a large number of possible reaction pathways.

The second phase includes the synthesis of the target material, which includes researchers performing hands-on laboratory work in order to synthesize, purify, and characterize the target material and precursory materials. During the second phase, researchers typically encounter difficulty or failure of one or more synthetic steps. The third phase typically requires researchers to make time-consuming adjustments to reaction/purification conditions and may even require alteration of a significant portion of the synthetic pathway. Each of these three phases can be highly time and labor intensive and can require a significant investment of personnel hours. Hence, there is a need for streamlining and automating each of these phases.

While prior work exists in the development of automated synthesizing machines and instruments, such set-ups have been developed for narrow types of chemistry. For example, there has been prior work in the areas of automated carbohydrate synthesis, automated peptide synthesis, and automated synthesis of large molecules using organic acid molecules containing boron (also referred to as MIDA boronates). In addition to the lack of scientific breadth, such automated synthesizers also require reaction planning, monitoring, and problem solving by human operators. Further, such narrowly focused automated synthesizers do not enable monitoring of reaction progress, in-situ planning, or troubleshooting.

SUMMARY

According to an embodiment, a process includes receiving information associated with a target molecule to be synthesized via a synthetic pathway engine user interface. The process also includes determining, using a synthetic pathway engine, synthetic pathway data for synthesis of the target molecule. The process further includes generating a synthetic pathway report user interface that includes information associated with the synthetic pathway data.

According to another embodiment, a process includes receiving information associated with a target molecule to be synthesized via a synthetic pathway engine user interface. The process also includes determining, using a synthetic pathway engine, synthetic pathway data for synthesis of the target molecule. The process further includes initiating automated synthesis of the target molecule using automated chemical synthesis equipment according to the synthetic pathway data.

According to another embodiment, a process includes receiving information associated with a target molecule to be synthesized via a synthetic pathway engine user interface. The process also includes determining, using a synthetic pathway engine, synthetic pathway data for synthesis of the target molecule. The process further includes generating a synthetic pathway report user interface that includes information associated with the synthetic pathway data. The process also includes initiating automated synthesis of the target molecule using automated chemical synthesis equipment, according to the synthetic pathway data, responsive to an input confirming acceptance of the synthetic pathway data.

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes a synthetic pathway engine that is utilized to design molecular synthesis pathways that satisfy certain criteria. As used herein, the term "synthetic pathway engine" is used to refer to software, hardware, or a combination thereof that is configured to perform various operations described herein. In the present disclosure, the synthetic pathway engine includes analytics functions that may enable streamlining of the research and development process, significantly shortening the planning and problem solving phases of development. The present disclosure combines analytical computation tools with automated synthesis technology to broaden the scope of automated chemical synthesis beyond the narrowly focused prior art solutions. Further, in some cases, automated synthesizing machines available to the synthetic pathway engine may be utilized to target general or specified synthetic goals. Illustrative, non-limiting examples of such targeted synthetic goals may include green chemistry (i.e., utilizing renewable resources), chemical methodology, screening of multiple catalysts or enzymes, total synthesis of pharmaceuticals, complex carbohydrate synthesis, DNA/peptide synthesis, or variations and combinations thereof.

In the present disclosure, synthetic pathway engine technology surveys the scientific literature to design synthetic pathways to complex molecules based on user-identified criteria. The synthetic pathway engine may operate in an "online" mode or an "offline" mode. In the offline mode, a synthetic pathway engine develops a synthetic route based on user inputs (e.g., maximum yield, minimum steps, available reagents, etc.) and generates a report that identifies the synthetic options to achieve the target molecule. In the online mode, the synthetic pathway engine may be integrated to a chemical synthesizer machine, which may include equipment such as reservoirs of reagents, catalyst, etc., automated mechanisms to siphon reagents into reactors, instrumentation to monitor reactions, and purification systems. Hence, in the online mode, the synthetic pathway engine conceptualizes and completes automated synthesis of target molecules. Further, the disclosure encompasses the combination of discovery of chemical pathways, automated synthesis, and a feedback mechanism by which the system can learn from both final results and intermediate steps.

In some cases, the synthetic pathway engine technology may enable a change to intermediate steps during an automated chemical synthesis procedure. This embodiment allows for capture of intermediate products/information as well as being able to alter the chemical synthesis procedure in real time based on the synthetic pathway engine technology knowledge.

Figure 1:
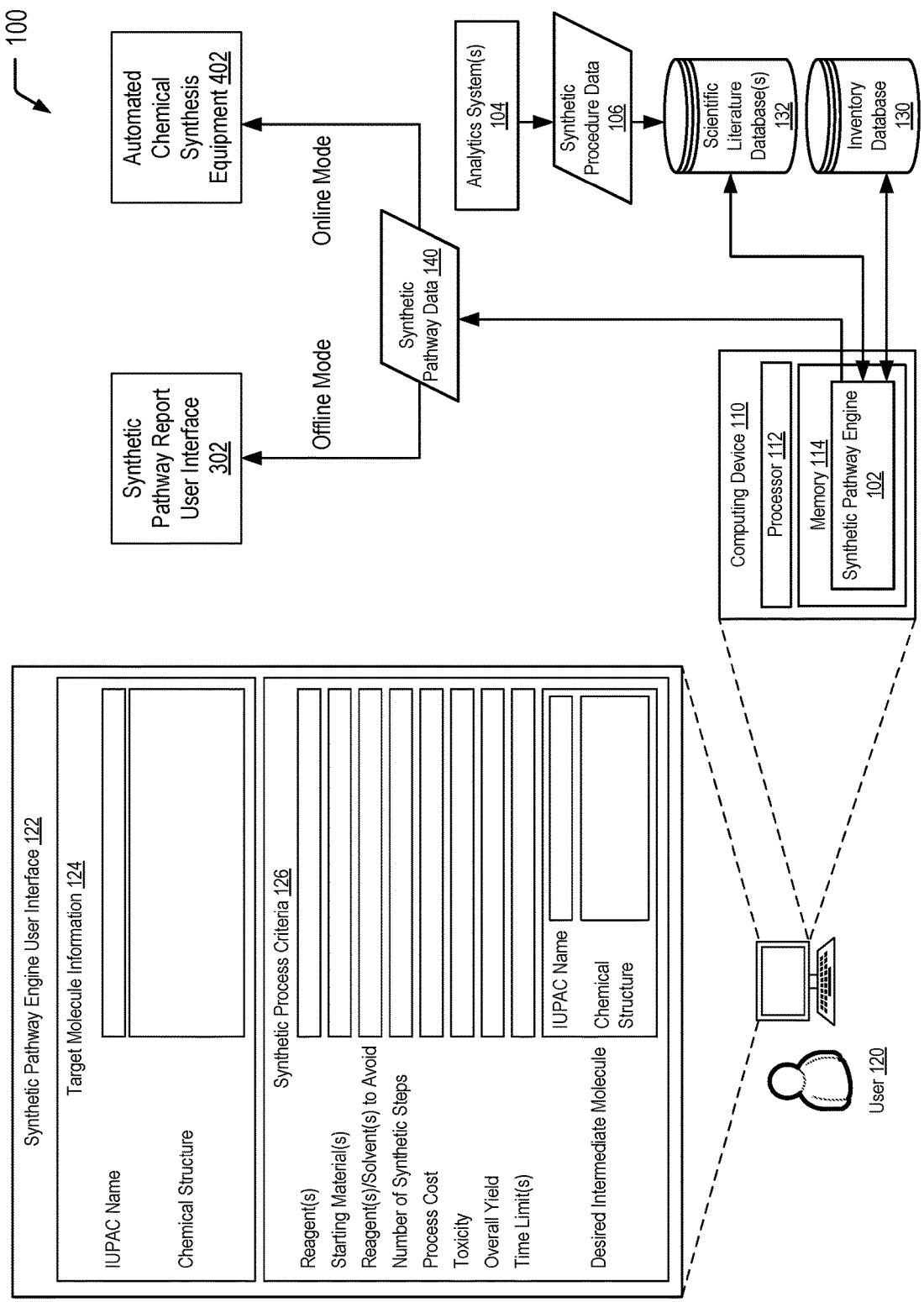
FIG. 1 is a block diagram of a system that includes a synthetic pathway engine that generates a synthetic pathway to a target molecule, according to one embodiment.

Referring to FIG. 1, a block diagram 100 illustrates an example of a system that includes a synthetic pathway engine 102, according to a particular embodiment. FIG. 1 illustrates that the synthetic pathway engine 102 may be utilized to identify one or more possible synthetic pathways to a particular target molecule based on synthetic procedure data 106 extracted from scientific literature using one or more analytics systems 104. As described further herein with respect to FIG. 3, in an offline mode, a synthetic pathway (or multiple possible synthetic pathways) that are identified by the synthetic pathway engine 102 may be presented as a report for user evaluation. As described further herein with respect to FIG. 4, in an online mode, a machine that includes synthesis equipment may enable automated synthesis of the target molecule according to the synthetic pathway designed by the synthetic pathway engine 102.

In the example of FIG. 1, a computing device 110 includes a processor 112 communicatively coupled to a memory 114, and the synthetic pathway engine 102 is stored in the memory 114. The memory 114 stores instructions that are executable by the processor 112 to perform operations described herein with respect to the synthetic pathway engine 102. It will be appreciated that the computing device 110 depicted in FIG. 1 is for illustrative purposes only and that the synthetic pathway engine 102 may utilize a combination of computing resources (e.g., artificial intelligence analytics resources capable of efficiently analyzing enormous amounts of data). For illustrative purposes only, various hardware and software components of the analytics system(s) 104 have been omitted from FIG. 1.

FIG. 1 illustrates that a user 120 may utilize a synthetic pathway engine user interface 122 to enter target molecule information 124. For example, in some cases, the user 120 may provide an IUPAC (International Union of Pure and Applied Chemistry) name for the target molecule. As another example, in other cases, the user 120 may upload a drawing of the chemical structure of the target molecule. In the event that the user 120 uploads a drawing to identify the target molecule, a chemical structure search may be performed using one or more chemical structure databases, such as those provided by a chemical reagent supplier (e.g., where each chemical structure is associated with a unique Chemical Abstract Services (CAS) number), among other possible chemical structure searching tools. While not shown in FIG. 1, it will be appreciated that the computing device 110 may include a network interface to enable data to be obtained from one or more online resources (e.g., an online chemical structure search tool).

In the particular embodiment depicted in FIG. 1, the synthetic pathway engine user interface 122 enables the user 120 to specify synthetic process criteria 126 for the synthetic pathway engine 102 to utilize when formulating possible synthetic scheme(s). In the example of FIG. 1, the synthetic process criteria 126 include a list of reagents and/or starting materials to use for the synthesis. In some cases, such information may include a custom-made list defined by the user 120, while in other cases such information may include a preset list (e.g., a preset list of common and well-known reagents, a list of inexpensive reagents, or a list of renewable chemicals). FIG. 1 illustrates an example in which the synthetic pathway engine 102 is linked to a laboratory's current chemical inventory (stored at an inventory database 130) to select a synthetic scheme that is compatible with the current synthetic capabilities that are available to the user 120. In other cases, the availability of particular reagent(s)/solvent(s), laboratory equipment, etc. may be assumed to be available to the user 120 for purposes of identifying one or more possible synthetic pathways to the target molecule.

FIG. 1 further illustrates that the synthetic process criteria 126 may also include options for a list of materials to be avoided (e.g., particular reagents and/or solvents, etc.), a limit on a number of synthetic steps in a possible synthetic pathway to the target molecule, an ultimate cost of the process, and/or toxicity of reagents (e.g., an input for a minimum LD50 value or an exclusion of published lists of chemicals such as RoHS or California Proposition 65 lists). Other examples of the synthetic process criteria 126 include overall yield, individual step or overall time limits, or a desire for a specific intermediate molecule, among numerous other alternatives or combinations thereof. Similar to the target molecule information 124 described above, FIG. 1 illustrates that the user 120 may identify the desired intermediate molecule based on an IUPAC name or by uploading an image of the chemical structure for the desired intermediate molecule.

Based on the target molecule information 124 provided by the user 120 via the synthetic pathway engine user interface 122 (and optionally the synthetic process criteria 126 provided by the user 120), the synthetic pathway engine 102 analyzes data obtained by the analytics system(s) 104 and stored in one or more scientific literature databases 132 in order to identify desirable reactions, to analyze the reliability of various reactions (e.g., according to frequency of use and changes in use over time), and to predict reaction yields (and to provide the user 120 with reliability estimates for yield predictions). It will be appreciated that the scientific literature database(s) 132 may include information from numerous sources of chemical synthesis information, including not only scientific journal articles, but also patent applications and patent applications, among numerous other potential sources of information for analysis by the analytics system (s) 104. As described herein with respect to FIGS. 2A-2C, reaction conditions are typically available in the experimental section and/or in the supplementary information section of the chemical literature. The analytics system(s) 104 may include sophisticated analytics capabilities (such as an artificial intelligence data analytics system) to parse such information for various components in order to build a database of synthetic pathways that include each of these components.

For purposes of analysis of information stored in the scientific literature database(s) 132, the synthetic pathway engine 102 may have access to information known to one of ordinary skill in the art of chemical synthesis. Examples of such information may include a chemical ontology, a chemical labware/equipment ontology, a chemical procedure ontology, a chemical purification ontology, and a material/compound characterization ontology. Chemical ontology information may include a list of specific chemicals in inventory or that are commercially available. Chemical labware/equipment ontology information may include glassware, purification apparatus, and distillation column information. Chemical procedure ontology information may include reaction conditions such as time, temperature, mix, and reflux information, and chemical purification ontology information may include decant, separation, recrystallization, distillation, and chromatography information. Material/compound characterization ontology information may include instrumental analysis information and chromatography information. Other examples of information accessible to the synthetic pathway engine 102 may include a chemical teaching curriculum (e.g., textbooks, software for identifying a compound based on an image, online tutorials, safety protocols, etc.) and a collection of standard reactions (e.g., nucleophilic addition, substitution, condensation, oxidation/reduction, polymerization, etc.), among numerous other alternatives.

The synthetic pathway engine 102 is configured to generate synthetic pathway data 140 that is consistent with the target molecule information 124 and the optional synthetic process criteria 126 specified by the user 120. FIG. 1 illustrates that, in an offline mode, the synthetic pathway data 140 generated by the synthetic pathway engine 102 may be provided as a report to the user 120 via a synthetic pathway report user interface 302 (as illustrated and further described herein with respect to FIG. 3). In the event that a chemical is not listed in the inventory database 130, the synthetic pathway engine 102 may prompt the user 120 to order that chemical or to automatically order that chemical once the proposed synthetic pathway is approved by the user 120. FIG. 1 further illustrates that, in an online mode, the synthetic pathway data 140 generated by the synthetic pathway engine 102 may be provided to automated chemical synthesis equipment 402. As illustrated and further described herein with respect to FIG. 4, such equipment may include various reservoirs containing reagents/solvents to utilize in the synthesis, siphons leading from the reservoirs to chemical reaction chambers, and automated purification systems. Optionally, the equipment may be linked to instrumentation such as a gas chromatograph, a mass spectrometer, an automated thin-layer chromatography system, a nuclear magnetic resonance spectrometer, etc. in order to monitor reactions and to confirm product identity.

Thus, FIG. 1 illustrates an example of a system that includes a synthetic pathway engine that generates synthetic pathway data that is consistent with target molecule information and optional synthetic process criteria specified by a user. In an offline mode, such synthetic pathway data may be provided as a report for the user to review. In an online mode, such synthetic pathway data may be provided to a machine that includes equipment capable of automatically performing the chemical reaction(s) and purification step(s) identified by the synthetic pathway engine.

Figure 2A:
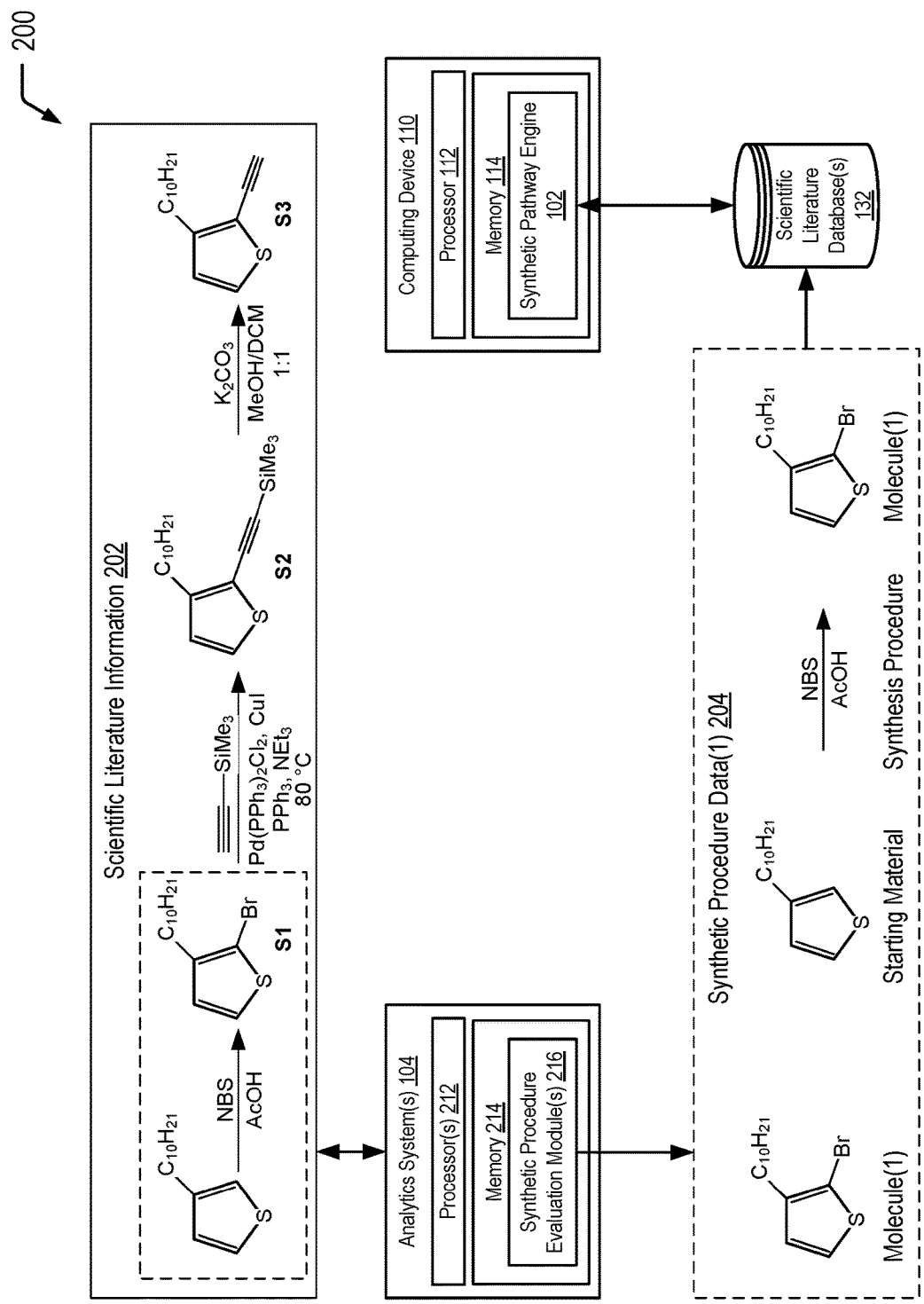
FIGS. 2A-2C are diagrams illustrating examples of reaction information from scientific literature that may be analyzed for use by the synthetic pathway engine in generating a synthetic pathway to a target molecule.
Figure 2B:
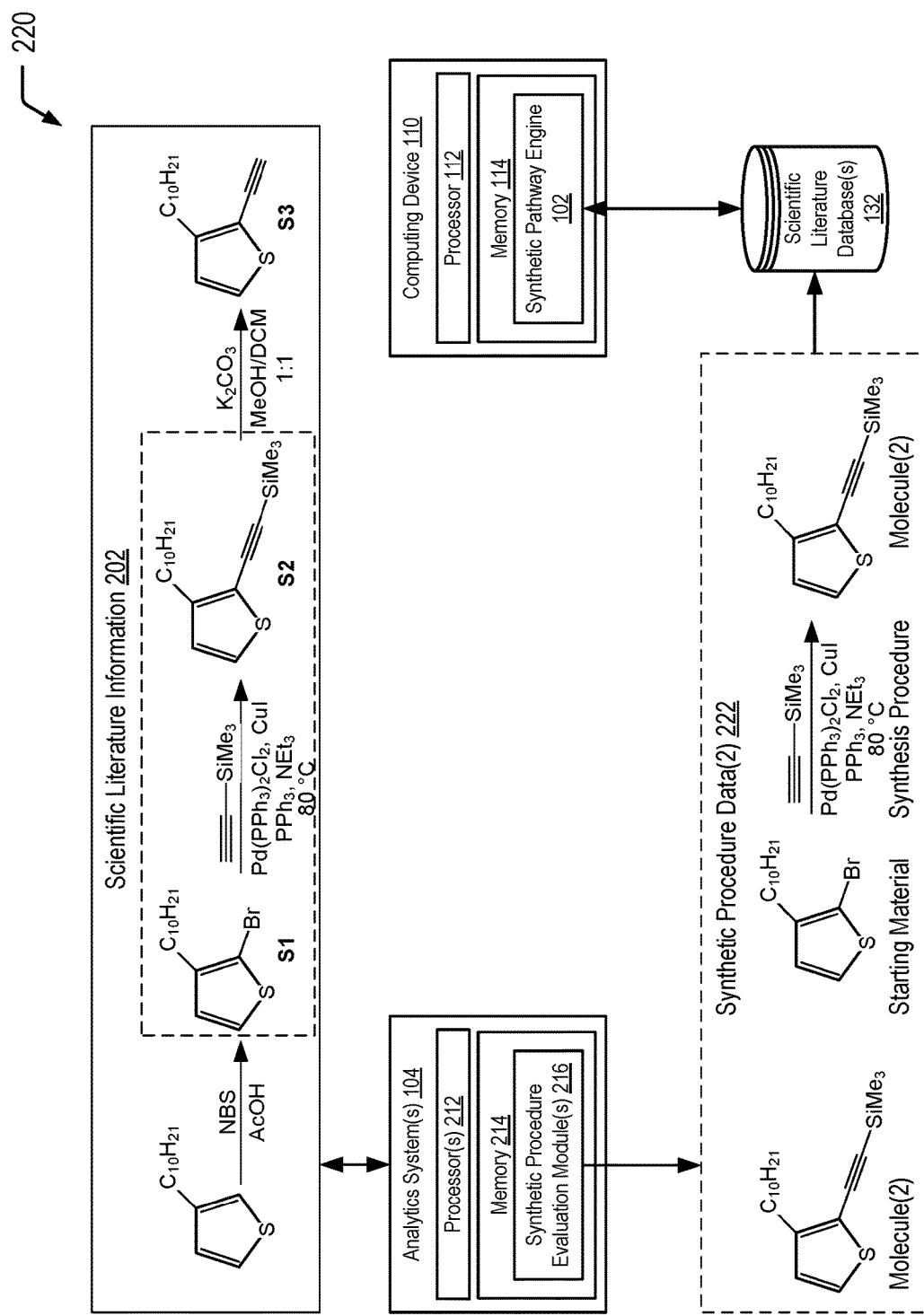
Figure 2C:
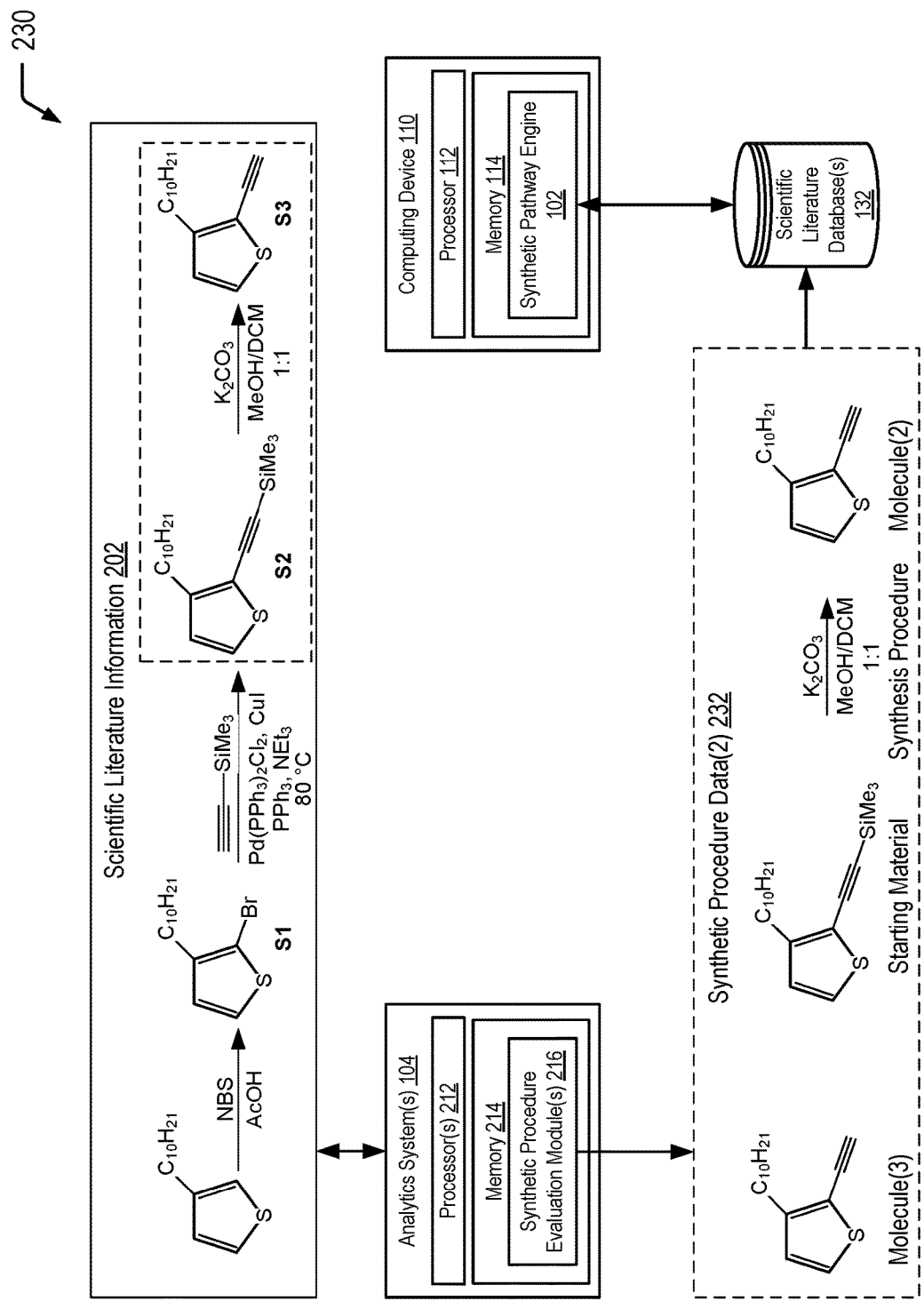

For illustrative purposes only, FIGS. 2A-2C are designed to illustrate examples of the type of reaction information that may be available in the experimental section and/or supplementary information section of a particular scientific literature article. Other reaction information may be contained within the text of the scientific literature article and can be extracted via the analytics system(s) 104. The synthetic pathway engine 102 may include or be linked to the analytics system(s) 104 that enable efficient analysis of numerous scientific literature articles in order to identify various molecules and various synthetic process pathways for forming such molecules. In some cases, such analytics system(s) 104 may include artificial intelligence components that are capable of reviewing an enormous breadth of scientific literature (e.g., more than 100 years of scientific literature). Thus, it will be appreciated that FIGS. 2A-2C depict one example of the type of information that may be extracted from a single scientific literature article. Further, it will be appreciated that the analytics system(s) 104 associated with the synthetic pathway engine 102 may include alternative and/or additional capabilities/methods of analyzing the enormous breadth of scientific literature that is available in the area of chemical synthesis procedures.

Referring to FIG. 2A, a diagram 200 illustrates an example of scientific literature information 202 that may be located in an experimental section and/or a supplementary information section of a scientific journal article (among other locations in other sources of chemical synthesis information).

In the example of FIG. 2A, the analytics system(s) 104 includes a processor 212 communicatively coupled to a memory 214, and one or more synthetic procedure evaluation modules 216 are stored in the memory 214. The memory 214 stores instructions that are executable by the processor 212 to perform operations described herein with respect to the synthetic procedure evaluation module(s) 216. It will be appreciated that the analytics system(s) 104 is illustrated in simplified form and may utilize a combination of computing resources (e.g., artificial intelligence analytics resources capable of efficiently analyzing enormous amounts of data). For illustrative purposes only, various hardware and software components of the analytics system(s) 104 have been omitted.

The synthetic procedure evaluation module(s) 216 analyze the scientific literature information 202 to extract synthetic procedure data 204 for the first product in the reaction scheme (identified as "S1" at the top of FIG. 2A). The analytics system(s) 104 stores the synthetic procedure data 204 associated the first product in the scientific literature database(s) 132 for subsequent utilization by the synthetic pathway engine 102 when identifying possible synthetic pathways for a particular target molecule identified by the user 102 via the synthetic pathway engine user interface 122 depicted in FIG. 1.

As an illustrative, non-limiting example of information that may be extracted for the first product, the scientific literature information 202 may include information that may be used to identify the chemical structure associated with the first product (S1) as 2-bromo-3-decylthiophene. The scientific literature information 202 may include the following information associated with the synthetic procedure to form 2-bromo-3-decylthiophene:

"To a stirred solution of 3-decylthiophene (21.10 g, 94 mmol) in 200 mL glacial acetic acid was added N-bromosuccinimide (16.73 g, 94 mmol) in one portion. The reaction mixture was stirred for 5 hours and diluted with 300 mL of water. The organic layer was extracted with hexane (×3) and the combined organics were washed subsequently with 1N NaOH, water and brine, then dried over $MgSO_4$. The solvents were removed in vacuo and the resulting crude product was purified by vacuum distillation to afford a pale yellow oil (27.0 g, 95%). $^1$H NMR (300 MHz; $CDCl_3$) δ 0.88 (3H, t, J=6.6), 1.24-1.34 (14H, m), 1.57 (2H, p), 2.56 (2H, t, J=7.7), 6.79 (d, J=5.7), 7.18 (d, 1H, J=5.6)."

Based on the synthetic procedure information, the synthetic procedure evaluation module(s) 216 may identify 3-decylthiophene as the starting material (and associated chemical structure) for the synthesis of 2-bromo-3-decylthiophene. FIG. 2A illustrates that the starting material (and associated chemical structure), the synthesis procedure, and the product (and associated chemical structure), may be stored in the scientific literature database(s) 132. Thus, in FIG. 2A, the analytics system(s) 104 identifies data related to the synthesis of one molecule (e.g., 2-bromo-3-decylthiophene), including a starting material (e.g., 3-decylthiophene), reaction conditions (e.g., stirring for 5 hours), solvents (e.g., glacial acetic acid, water), as well as subsequent purification steps and NMR analysis data for the molecule. As described further herein with respect to FIG. 2B, when the analytics system(s) 104 identifies other data associated with the first molecule, the data may be linked in the scientific literature database(s) 132 for subsequent use in a multi-step synthetic procedure for a particular target molecule.

Referring to FIG. 2B, a diagram 220 illustrates an example of additional data that may be extracted from the scientific literature information 202. In FIG. 2B, the synthetic procedure evaluation module(s) 216 analyzes the scientific literature information 202 to extract synthetic procedure data 222 for the second product in the reaction scheme (identified as "S2" at the top of FIG. 2B). The analytics system(s) 104 stores the synthetic procedure data 222 associated the second product in the scientific literature database(s) 132 for subsequent utilization by the synthetic pathway engine 102 when identifying possible synthetic pathways for a particular target molecule identified by the user 102 via the synthetic pathway engine user interface 122 depicted in FIG. 1.

Based on the synthetic procedure information, the synthetic procedure evaluation module(s) 216 may identify 2-bromo-3-decylthiophene (and associated chemical structure) as the starting material for the synthesis of the second product (S2). Additional information related to the procedure to synthesize the second product (S2) from 2-bromo-3-decylthiophene may also be extracted from the scientific literature information 202.

FIG. 2B illustrates that the starting material (and associated chemical structure), the synthesis procedure, and the product (and associated chemical structure) may be stored in the scientific literature database(s) 132. Thus, in FIG. 2B, the analytics system(s) 104 identifies additional data for the first molecule described with respect to FIG. 2A (i.e., 2-bromo-3-decylthiophene). Thus, the data stored in the scientific literature database(s) 132 identifies not only a synthetic pathway to the first molecule but also a synthetic pathway to another molecule (S2) when the first molecule is used as the starting material.

Referring to FIG. 2C, a diagram 230 illustrates an example of additional data that may be extracted from the scientific literature information 202. In FIG. 2C, the synthetic procedure evaluation module(s) 216 analyzes the scientific literature information 202 to extract synthetic procedure data 232 for the third product in the reaction scheme (identified as "S3" at the top of FIG. 2C). The analytics system(s) 104 stores the synthetic procedure data 232 associated the third product in the scientific literature database(s) 132 for subsequent utilization by the synthetic pathway engine 102 when identifying possible synthetic pathways for a particular target molecule identified by the user 102 via the synthetic pathway engine user interface 122 of FIG. 1.

Based on the synthetic procedure information, the synthetic procedure evaluation module(s) 216 may identify S2 (and associated chemical structure) as the starting material for the synthesis of the third product (S3). Additional information related to the procedure to synthesize the third product (S3) from the second product (S2) may also be extracted from the scientific literature information 202.

FIG. 2C illustrates that the starting material (and associated chemical structure), the synthesis procedure, and the product (and associated chemical structure) may be stored in the scientific literature database(s) 132. Thus, in FIG. 2C, the analytics system(s) 104 identifies additional data for the second molecule described with respect to FIG. 2B (i.e., "S2"). Thus, the data stored in the scientific literature database(s) 132 identifies not only a synthetic pathway to the second molecule but also a synthetic pathway to another molecule (S3) when the second molecule is used as the starting material. It will be appreciated that FIGS. 2A-2C depict examples of information that is extracted from a single reference and the analytics system(s) 104 may also analyze and log additional routes to similar molecules. Further, there may be other variations of conditions that produce such compounds (e.g., other solvents, bromine sources, catalysts, bases, etc.). In such cases, the results presented to the user 120 (e.g., via the synthetic pathway report user interface 302 depicted in FIG. 3) may be those that most closely match user preferences (e.g., as defined by the user 120 via the synthetic pathway engine user interface 122 depicted in FIG. 1).

Figure 3:
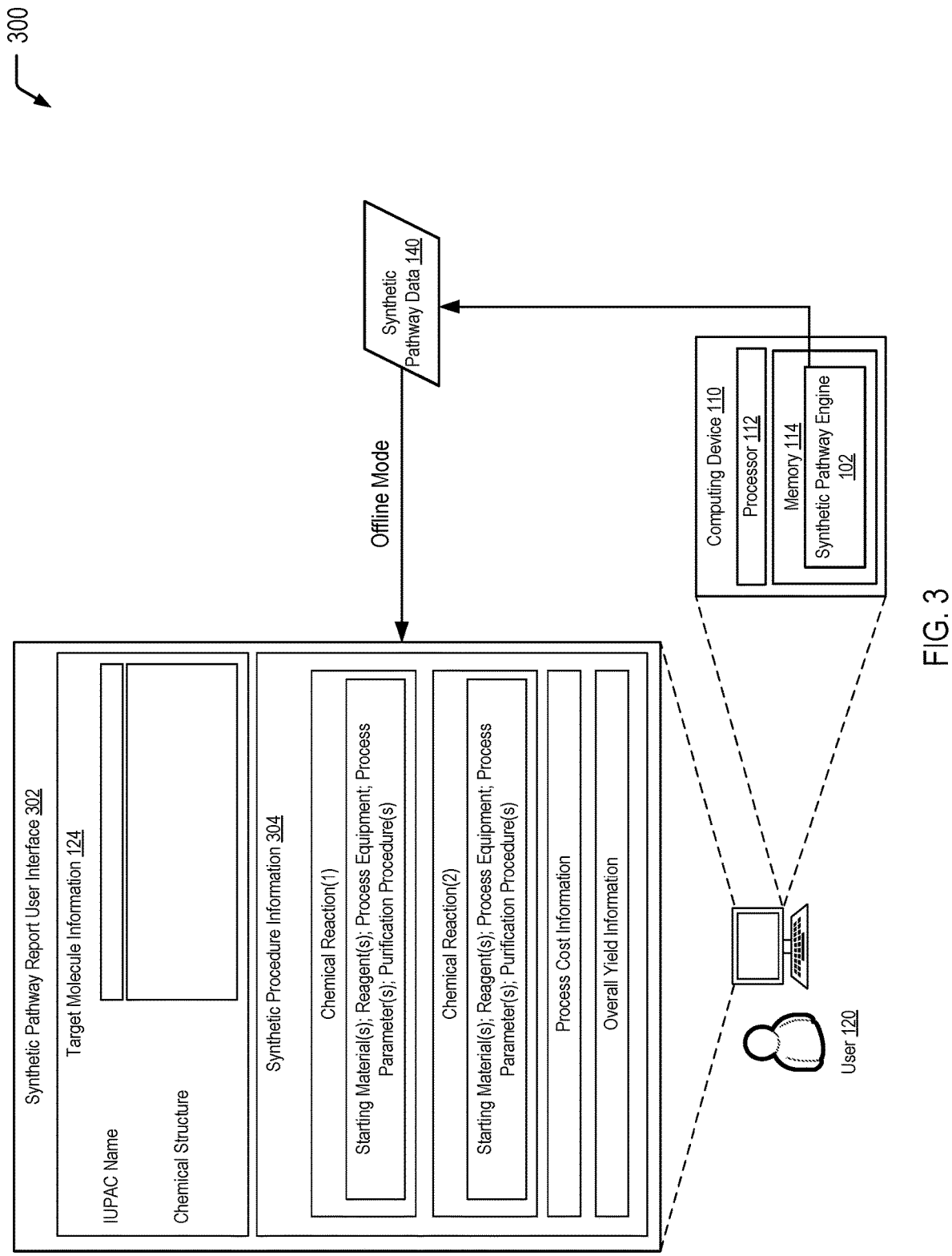
FIG. 3 is a block diagram illustrating an offline mode in which a synthetic pathway to a target molecule that is identified by the synthetic pathway engine is presented as a report for user review.

Referring to FIG. 3, a block diagram 300 illustrates that, in the offline mode, the user 120 may review the synthetic pathway data 140 generated by the synthetic pathway engine 102 using a synthetic pathway report user interface 302.

In the example illustrated in FIG. 3, the synthetic pathway report interface 302 includes an example of a report that identifies synthetic procedure information 304 for the target molecule (identified by the user 120 as the target molecule information 124 via the synthetic pathway engine user interface 122 of FIG. 1). The synthetic procedure information 304 may include information associated with multiple chemical reactions in the synthetic pathway and optionally may include other information that may assist the user 120 in evaluating the proposed synthetic pathway. To illustrate, in FIG. 3, information associated with each of the chemical reactions in the proposed synthetic pathway may include starting material(s), reagent(s), process equipment, process parameter(s), purification procedure(s), or various combinations thereof. For illustrative purposes only, FIG. 3 depicts an example in which the synthetic pathway includes two chemical reactions. It will be appreciated that more than two chemical reactions may be associated with a particular synthetic pathway and that information for multiple possible synthetic pathways generated by the synthetic pathway engine 102 may be presented for user evaluation. In some cases, an additional feature associated with the synthetic pathway report interface 302 may be to provide the user 120 with the ability to choose between multiple parallel options (such as two different sets of chemical reactions to make the same molecules) along with series options.

In the particular embodiment illustrated in FIG. 3, the synthetic procedure information 304 further includes process cost information and overall yield information, among other possible information such as a list of references from which the chemical reaction information was extracted/derived. Such information may be useful to the user 120 in evaluating the viability of a particular synthetic pathway. It will be appreciated that alternative and/or additional information may be presented to the user 120 in other embodiments. Further, while not shown in FIG. 3, in some cases, the synthetic pathway report user interface 302 may enable the user 120 to instruct the synthetic pathway engine 102 to initiate the automated synthesis of the target molecule using the automated synthesis equipment 402, as described further herein with respect to FIG. 4.

Thus, FIG. 3 illustrates an example of a report that may be presented to a user that includes information associated with a proposed synthetic pathway that is identified by a synthetic pathway engine for a particular target molecule. In some cases, the user may iteratively adjust the parameters provided via the synthetic pathway engine user interface 122 of FIG. 1 based on the information in the report. In other cases, the synthetic pathway may be utilized to automatically synthesize the target molecule, as illustrated and further described herein with respect to FIG. 4.

Figure 4:
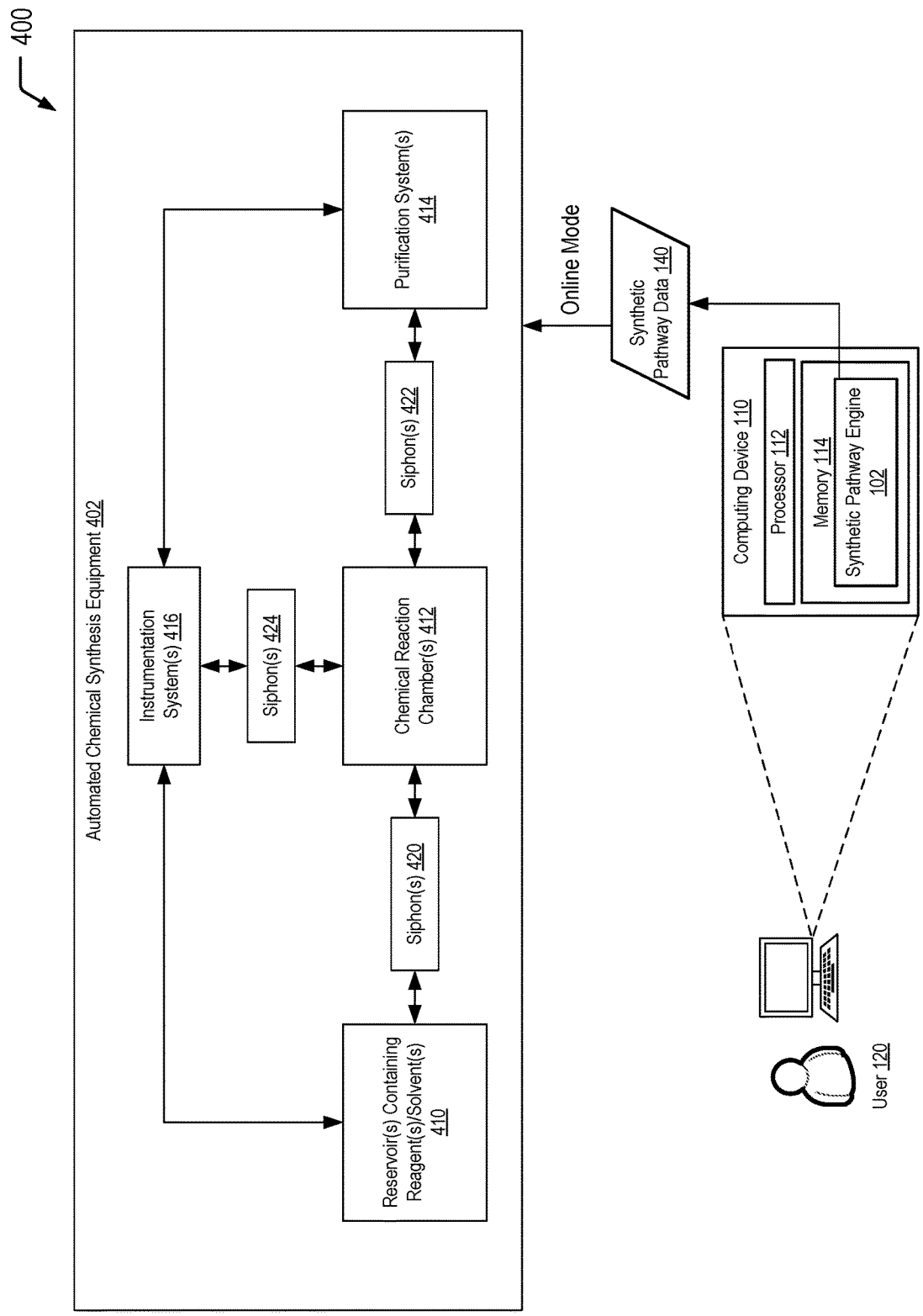
FIG. 4 is a block diagram illustrating an online mode in which a synthetic pathway engine is coupled to a machine that enables automated chemical synthesis of a target molecule based on the synthetic pathway to the target molecule identified by the synthetic pathway engine.

Referring to FIG. 4, a block diagram 400 illustrates that, in the online mode, the user 120 may utilize the synthetic pathway data 140 generated by the synthetic pathway engine 102 to automatically synthesize the target molecule using the automated chemical synthesis equipment 402.

In the example illustrated in FIG. 4, the automated chemical synthesis equipment 402 includes one or more reservoirs 410, one or more chemical reaction chambers 412, and one or more purification systems 414. The purification system(s) 414 may include, but is not limited to, an automated extractor and/or automated flash chromatography system. In the particular embodiment depicted in FIG. 4, the automated chemical synthesis equipment 402 further includes one or more instrumentation systems 416. Examples of instrumentation systems may include Fourier transform infrared spectroscopy (FTIR) instruments, gas chromatography/mass spectroscopy (GC/MS) instruments, thin-layer chromatography (TLC) instruments, among numerous other alternatives.

FIG. 4 illustrates that one or more siphons 420 may be utilized to siphon material(s) from the reservoir(s) 410 to the chemical reaction chamber(s) 412, one or more siphons 422 may be utilized to siphon reaction product(s) to the purification system(s) 414, and one or more siphons 424 may be utilized to siphon reaction product(s) to the instrumentation system(s) 416. Additionally, while not shown in the example depicted in FIG. 4, aliquots removed from the chemical reaction chamber(s) 412 may be purified before being delivered to the instrumentation system(s) 416. As another example, while not shown the example depicted in FIG. 4, the reaction product(s) may be diluted/dissolved prior to being delivered to the instrumentation system(s) 416. The reservoir(s) 410 may contain one or more reagents, one or more solvents, one or more starting molecules, or combinations thereof, among other alternatives. In some cases, the reservoir(s) 410 may contain either a preset list of reagents or may remain empty initially, and the user 120 may be prompted to manually fill the reservoir(s) 410 with a list of reagents suggested by the synthetic pathway engine 102 that are required to initiate the reaction(s).

Upon user review and confirmation of the synthetic route to the target molecule, the synthetic pathway engine 102 provides instructions to the automated chemical synthesis equipment 402 to initiate siphoning of reagents to reactors with temperature and stirring control, online monitoring of reactions, and siphoning of the crude products to purification systems. Throughout the course of the synthesis, product and side-product formation are monitored using one or more of the instrumentation system(s) 416. With regard to the side-product formation, the synthetic pathway engine 102 may log the side-product species and reaction conditions/materials as well as determine if there may be other uses for the particular side-product. In some cases, in the online mode, such information may be available to an open database that allows other users to communicate. For example, another organization may be attempting to synthesize a particular molecule that requires a unique chemical that happens to be a side-product formed using the automated chemical synthesis equipment 402. Chemical synthesis information associated with the particular side-product may be provided to the other organization (e.g., for a fee), potentially representing an additional revenue stream that may be associated with a particular synthetic pathway. As another example, the synthetic pathway engine 102 may be capable of reviewing patent applications and/or patents (among other potential sources of information) to determine whether a particular side-product represents a novel composition of matter. Alternatively, the user 120 may search for the particular side-product in a known literature/structure database to determine whether the side-product represents a novel composition of matter.

In the case of unforeseen problems, the synthetic pathway engine 102 has the ability to either preliminarily end the reaction in order to preserve starting material for a subsequent attempt or to attempt an in-situ injection of custom reagents designed to improve yields. As an example of real time adjustment of a chemical reaction, the synthetic pathway engine 102 may identify a reduction/cessation of catalytic activity (such as in a palladium-catalyzed system, such as the synthesis of S3 from S2, as depicted in FIG. 2C). To illustrate, the catalyst may become oxidizing or may have exceeded its turn-over number. In response, the synthetic pathway engine 102 may add more catalyst to the chemical reaction chamber(s) 412. As another example, a chemical reaction may utilize a strong base (such as n-Butyllithium) to deprotonate a molecule. Typically, a user would add a slight excess of the base to ensure that all of the desired protons are removed. However, if complete deprotonation is critical, the user typically removes a small aliquot of material from the reaction, quenches it either with a deuterium source ($D_2O$), an electrophile, and then performs the relevant analysis to check for completion of the deprotonation (e.g., using NMR, GC/MS, etc.). The automated chemical synthesis equipment 402 may enable the automation of such a procedure. As yet another example, a chemical that is unexpected based on the synthetic pathway engine's analytics may be liberated throughout the course of the reaction. In the event that the synthetic pathway engine 102 deems the chemical to be detrimental to the reaction process, the synthetic pathway engine 102 may have the ability to identify the chemical concurrent to its generation, search the broad scientific literature for potential resolutions, and apply such a resolution that reduces the detrimental effect on the desired reaction, such as releasing additional reagent designed to chemically quench the unexpected and detrimental chemical. While not shown in FIG. 4, after completion of the synthesis of the target molecule, the synthetic pathway engine 102 may provide the user with a report that includes the actual reaction conditions applied, actual yield for individual steps, among other possible information.

Thus, FIG. 4 illustrates an example in which the synthetic pathway data generated by the synthetic pathway engine may be utilized to automatically synthesize a particular target molecule using automated chemical synthesis equipment. In the example depicted in FIG. 4, the automated chemical synthesis equipment includes one or more instrumentation systems that may be used to monitor product and side-product formation throughout the course of the synthesis.

Figure 5:
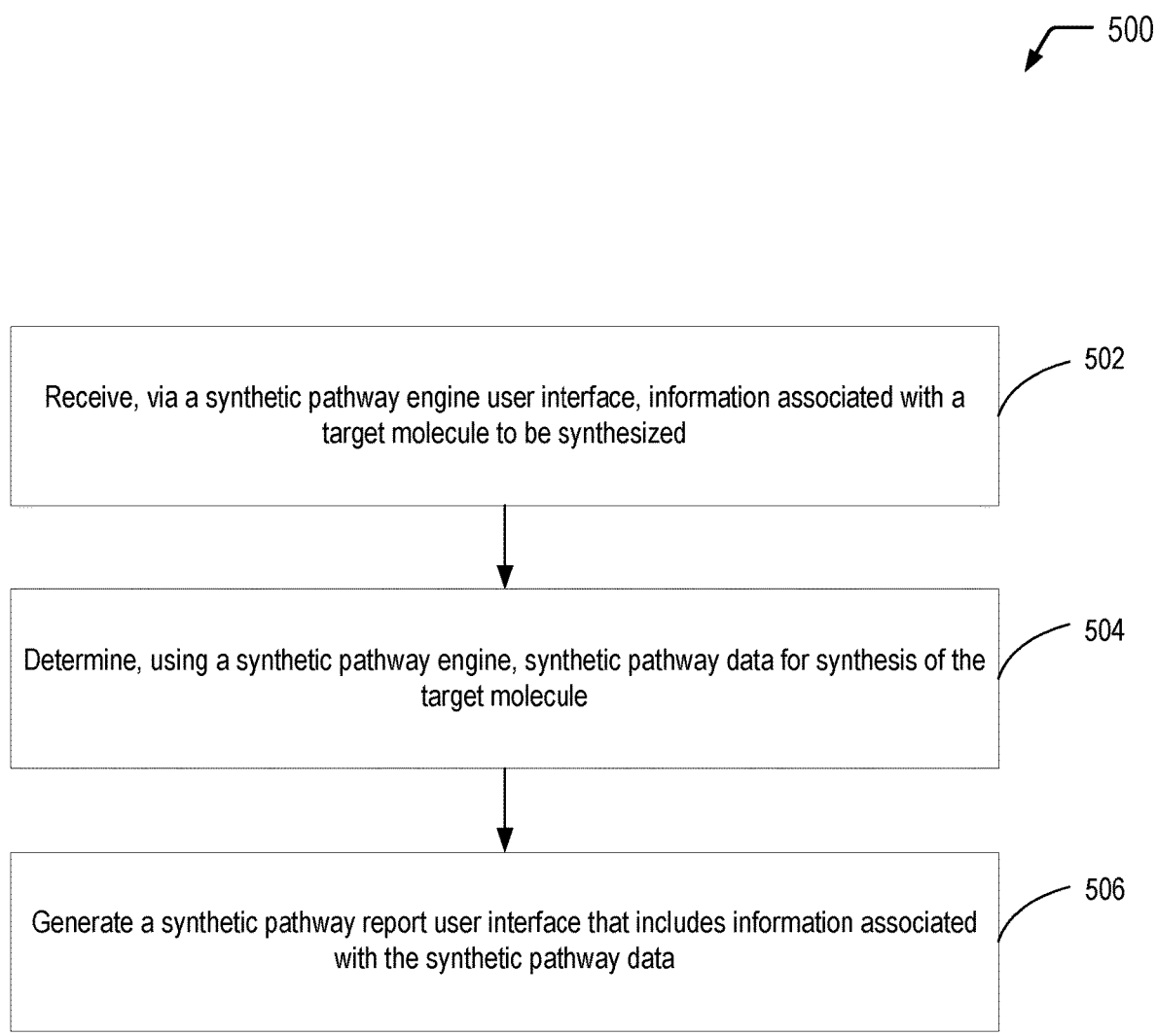
FIG. 5 is a flow diagram showing a particular embodiment of a process of utilizing a synthetic pathway engine in an offline mode to generate a synthetic pathway report user interface that includes synthetic pathway data identified for a target molecule.

Referring to FIG. 5, a flow diagram illustrates a particular embodiment of a process 500 of utilizing a synthetic pathway engine to generate a synthetic pathway report user interface that includes information associated with synthetic pathway data that is determined using the synthetic pathway engine of the present disclosure. FIG. 5 represents an example of the utilization of the synthetic pathway engine of the present disclosure in an offline mode, whereby a user is presented with a report that includes details associated with a proposed synthetic pathway for review.

The process 500 includes receiving information associated with a target molecule to be synthesized, at 502. The information associated the target molecule may be received via a synthetic pathway engine user interface. For example, referring to FIG. 1, the user 120 may provide the target molecule information 124 via the synthetic pathway engine user interface 122. In some cases, the target molecule information 124 may include an IUPAC name of the target molecule. In other cases, the target molecule information 124 may include an image of a chemical structure of the target molecule. In some cases, the user 120 may also provide the synthetic process criteria 126 via the synthetic pathway engine user interface 122.

The process 500 includes determining, using a synthetic pathway engine, synthetic pathway data for synthesis of the target molecule, at 504. For example, referring to FIG. 1, based on the target molecule information 124 provided by the user 120 (and optionally the synthetic process criteria 126), the synthetic pathway engine 102 may identify the synthetic pathway data 140 for the target molecule. The synthetic pathway data 140 may be determined based on information obtained by the analytics system(s) 104 based on a review of scientific literature, as described further herein with respect to FIGS. 2A-2C.

The process 500 includes generating a synthetic pathway report user interface that includes information associated with the synthetic pathway data, at 506. For example, referring to FIG. 3, the synthetic pathway data 140 generated by the synthetic pathway engine 102 may be used to generate the synthetic pathway report user interface 302. The synthetic pathway report user interface 302 identifies the synthetic procedure information 304 associated with a possible synthetic pathway to the target molecule, thereby providing the user 120 with an opportunity to review the proposed synthetic procedure. Optionally, after review the synthetic procedure information 304, the user 120 may utilize the synthetic pathway engine user interface 122 of FIG. 1 to provide alternative or additional synthetic process criteria 126 that may result in alternative or additional synthetic pathways to the target molecule.

Thus, FIG. 5 illustrates an example of a process of utilizing the synthetic pathway engine of the present disclosure in an offline mode. In the offline mode, a user is presented with a report that provides details regarding a possible synthetic pathway to a target molecule.

Figure 6:
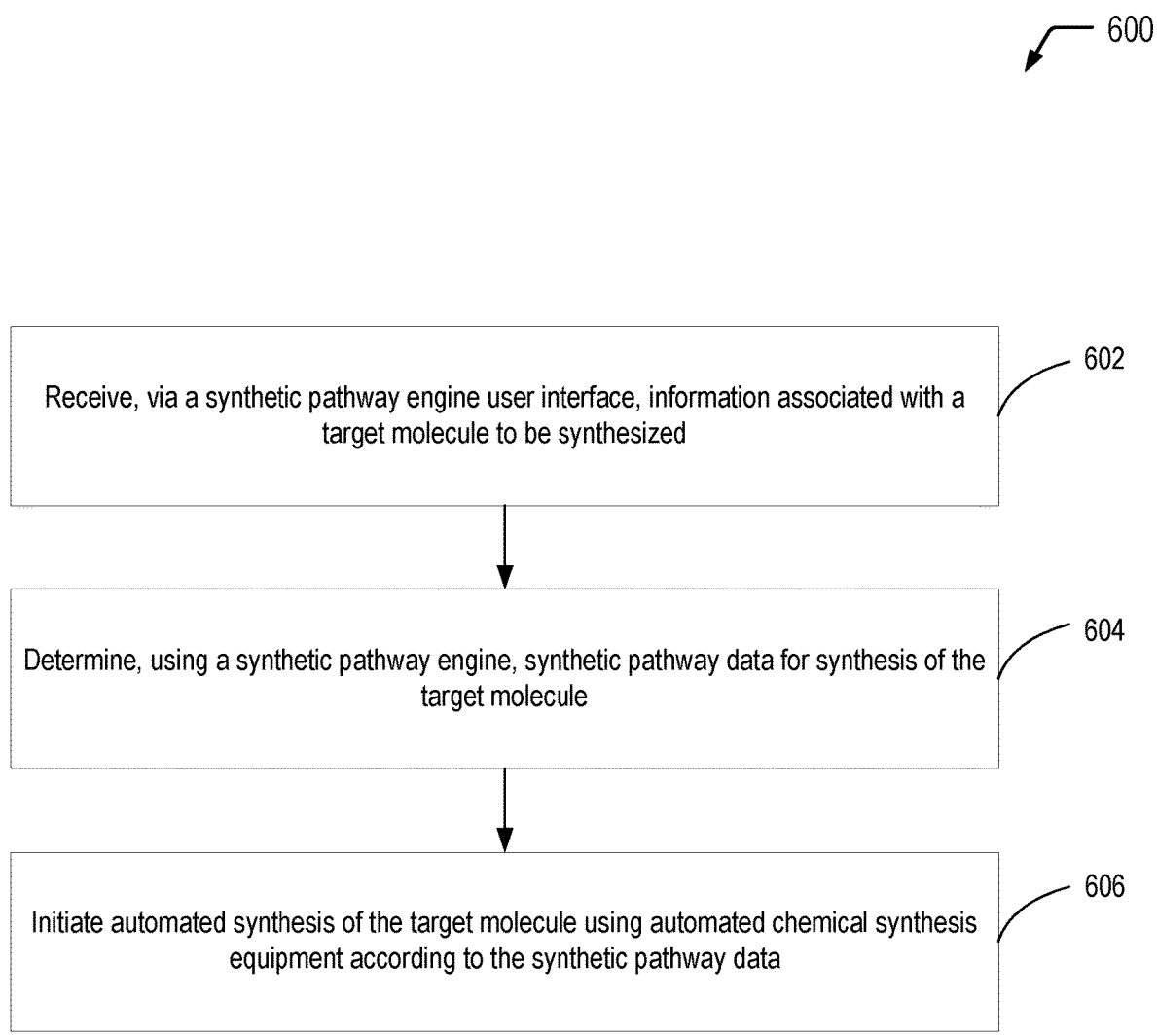
FIG. 6 is a flow diagram showing a particular embodiment of a process of utilizing a synthetic pathway engine in an online mode to automatically synthesize a target molecule based on synthetic pathway data identified for the target molecule.

Referring to FIG. 6, a flow diagram illustrates a particular embodiment of a process 600 of utilizing a synthetic pathway engine to automatically synthesize a target molecule based on synthetic pathway data that is determined using the synthetic pathway engine. FIG. 6 represents an example of the utilization of the synthetic pathway engine of the present disclosure in an online mode utilizing automated chemical synthesis equipment to synthesize the target molecule.

The process 600 includes receiving information associated with a target molecule to be synthesized, at 602. The information associated the target molecule may be received via a synthetic pathway engine user interface. For example, referring to FIG. 1, the user 120 may provide the target molecule information 124 via the synthetic pathway engine user interface 122. In some cases, the target molecule information 124 may include an IUPAC name of the target molecule. In other cases, the target molecule information 124 may include an image of a chemical structure of the target molecule. In some cases, the user 120 may also provide the synthetic process criteria 126 via the synthetic pathway engine user interface 122.

The process 600 includes determining, using a synthetic pathway engine, synthetic pathway data for synthesis of the target molecule, at 604. For example, referring to FIG. 1, based on the target molecule information 124 provided by the user 120 (and optionally the synthetic process criteria 126), the synthetic pathway engine 102 may identify the synthetic pathway data 140 for the target molecule. The synthetic pathway data 140 may be determined based on information obtained by the analytics system(s) 104 based on a review of scientific literature, as described further herein with respect to FIGS. 2A-2C.

The process 600 includes initiating automated synthesis of the target molecule using automated chemical synthesis equipment according to the synthetic pathway data, at 606. For example, referring to FIG. 4, the automated chemical synthesis equipment 402 may synthesize the target molecule based on the synthetic pathway data 140 generated by the synthetic pathway engine 102.

Thus, FIG. 6 illustrates an example of a process of utilizing the synthetic pathway engine of the present disclosure in an online mode. In the online mode, automated chemical synthesis equipment is utilized to synthesize a target molecule based on a synthetic pathway identified by the synthetic pathway engine.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A computer-implemented method for developing new materials through chemical synthesis, wherein a processor of a computing device that is communicatively coupled to automated chemical synthesis equipment is programmed to execute software instructions that cause the processor to perform the computer-implemented method, the computer-implemented method comprising:

receiving, by the processor via a communicatively coupled synthetic pathway engine user interface, information associated with a target molecule to be synthesized;

determining, by the processor using a synthetic pathway engine stored in the computing device, synthetic pathway data by analyzing synthetic procedure data that is stored in one or more communicatively coupled databases, wherein the synthetic procedure data was extracted by one or more analytics systems from scientific literature stored in the one or more communicatively coupled databases, wherein the synthetic pathway data comprises synthetic procedure information for synthesis of the target molecule;

generating, by the processor, a synthetic pathway report user interface that includes information associated with the synthetic pathway data, wherein the information associated with the synthetic pathway data comprises input for one or more starting materials, one or more process equipment, one or more process parameters, and one or more procedures for synthesizing the target molecule; and initiating, by the processor, automated synthesis of the target molecule using the communicatively coupled automated chemical synthesis equipment according to the synthetic pathway data, wherein the automated chemical synthesis equipment includes one or more reservoirs, one or more chemical reaction chambers, and one or more purification systems.

2. The computer-implemented method of claim 1, wherein the one or more purification systems include an automated extractor, an automated flash chromatography system, or a combination thereof.

3. The computer-implemented method of claim 1, wherein the automated chemical synthesis equipment further includes one or more instrumentation systems.

4. The computer-implemented method of claim 3, wherein the one or more instrumentation systems include a Fourier transform infrared spectroscopy (FTIR) instrument, a gas chromatography/mass spectroscopy (GC/MS) instrument, a thin-layer chromatography (TLC) instrument, or a combination thereof.

5. A computer-implemented method for developing new materials through chemical synthesis, wherein a processor of a computing device that is communicatively coupled to automated chemical synthesis equipment is programmed to execute software instructions that cause the processor to perform the computer-implemented method, the computer-implemented method comprising:

receiving, by the processor via a communicatively coupled synthetic pathway engine user interface, information associated with a target molecule to be synthesized;

determining, by the processor using a synthetic pathway engine stored in the computing device, synthetic pathway data by analyzing synthetic procedure data that is stored in one or more communicatively coupled databases, wherein the synthetic procedure data was extracted by one or more analytics systems from scientific literature, patent applications, or patents located on the one or more communicatively coupled databases, wherein the synthetic pathway data comprises synthetic procedure information for synthesis of the target molecule;

generating, by the processor, a synthetic pathway report user interface that includes information associated with the synthetic pathway data, wherein the information associated with the synthetic pathway data comprises input for one or more starting materials, one or more process equipment, one or more process parameters, and one or more procedures for synthesizing the target molecule;

receiving, by the processor, an input confirming acceptance of the synthetic pathway data; and initiating, by the processor, automated synthesis of the target molecule using communicatively coupled automated chemical synthesis equipment according to the synthetic pathway data, wherein the automated chemical synthesis equipment includes one or more reservoirs, one or more chemical reaction chambers, one or more purification systems, and one or more instrumentation systems.

6. The computer-implemented method of claim 5, further comprising:

receiving, by the processor, results associated with synthesis of the target molecule according to the synthetic pathway data from one or more instrumentation systems coupled to the automated chemical synthesis equipment; and displaying, by the processor, the results on the synthetic pathway report user interface.

7. The computer-implemented method of claim 6, wherein the results include product formation information, side-product formation information, or a combination thereof.

8. The computer-implemented method of claim 6, wherein the results include information associated with one or more unexpected chemicals that are generated during synthesis of the target molecule.

9. The computer-implemented method of claim 1, further comprising receiving synthetic process criteria via the synthetic pathway engine user interface, wherein the synthetic process criteria narrows the determining of the synthetic pathway data.

10. The computer-implemented method of claim 1, wherein the synthetic process criteria include at least one of:

one or more references that include information related to synthesis of one or more intermediate compounds or one or more final products;

one or more reagents to be utilized for synthesis of the target molecule;

one or more materials to be excluded for synthesis of the target molecule;

a number of synthetic steps to be performed during synthesis of the target molecule;

a process cost associated with synthesis of the target molecule;

toxicity information associated with materials utilized for synthesis of the target molecule;

an overall yield associated with synthesis of the target molecule;

one or more time limits associated with synthesis of the target molecule; and a desired intermediate molecule.

11. The computer-implemented method of claim 1, further comprising:

receiving, by the processor via the synthetic pathway engine user interface, synthetic process criteria inputted by a user, wherein the synthetic process criteria includes a list of starting materials for synthesizing the target molecule;

determining, by the processor using the synthetic pathway engine, availability of the starting materials by accessing a communicatively coupled inventory database; and filtering, by the processor using the synthetic pathway engine, the information associated with the synthetic pathway data according to the availability of the starting materials.

12. The computer-implemented method of claim 1, wherein receiving information associated with the target molecule to be synthesized comprises:
    receiving, by the processor via the synthetic pathway engine user interface, an image of a drawing representing the chemical structure of the target molecule;
    identifying, by the processor using the synthetic pathway engine, the target molecule by matching the image of the drawing to known chemical structures by searching a communicatively coupled chemical structure database.

13. The computer-implemented method of claim 1, wherein the one or more analytics systems are artificial intelligence systems.

14. The computer-implemented method of claim 1, wherein the automated chemical synthesis equipment includes a chemical reaction chamber where the target molecule is synthesized via a chemical reaction, the method further comprising:
    monitoring, by the processor using the synthetic pathway engine and one or more communicatively coupled instrumentation systems, the ongoing synthesis of the target molecule for product and side-product formation, and for formation of unexpected molecules;
    identifying, by processor using the synthetic pathway engine and in response to determining that one or more unexpected molecules have been formed, one or more chemical agents that can be added to the chemical reaction to reduce a detrimental effect of the one or more unexpected molecules on the synthesis of the target molecule; and
    adjusting, by the processor using the synthetic pathway engine, the synthesis of the target molecule by injecting the one or more chemical agents into the chemical reaction chamber.

15. The computer-implemented method of claim 1, wherein the automated chemical synthesis equipment includes a chemical reaction chamber where the target molecule is synthesized via a chemical reaction, the method further comprising:
    removing, by the processor using the automated chemical synthesis equipment, an aliquot of material from chemical reaction;
    determining, by the processor using the synthetic pathway engine and the automated chemical synthesis equipment, whether the aliquot satisfies one or more user-criteria for the target molecule; and
    adjusting, by the processor using the synthetic pathway engine and in response to determining that the aliquot does not satisfy the one or more criteria for the target molecule, the synthesis of the target molecule.

16. The computer-implemented method of claim 5, further comprising:
    receiving, by the processor via the synthetic pathway engine user interface, synthetic process criteria inputted by a user, wherein the synthetic process criteria includes a list of starting materials for synthesizing the target molecule;
    determining, by the processor using the synthetic pathway engine, availability of the starting materials by accessing a communicatively coupled inventory database; and
    filtering, by the processor using the synthetic pathway engine, the information associated with the synthetic pathway data according to the availability of the starting materials.

17. The computer-implemented method of claim 5, wherein receiving information associated with the target molecule to be synthesized comprises:
    receiving, by the processor via the synthetic pathway engine user interface, an image of a drawing representing the chemical structure of the target molecule;
    identifying, by the processor using the synthetic pathway engine, the target molecule by matching the image of the drawing to known chemical structures by searching a communicatively coupled chemical structure database.

18. The computer-implemented method of claim 5, wherein the one or more analytics systems are artificial intelligence systems.

19. The computer-implemented method of claim 5, wherein the automated chemical synthesis equipment includes a chemical reaction chamber where the target molecule is synthesized via a chemical reaction, the method further comprising:
    monitoring, by the processor using the synthetic pathway engine and the one or more instrumentation systems, the ongoing synthesis of the target molecule for product and side-product formation, and for formation of unexpected molecules;
    identifying, by processor using the synthetic pathway engine and in response to determining that one or more unexpected molecules have been formed, one or more chemical agents that can be added to the chemical reaction to reduce a detrimental effect of the one or more unexpected molecules on the synthesis of the target molecule; and
    adjusting, by the processor using the synthetic pathway engine, the synthesis of the target molecule by injecting the one or more chemical agents into the chemical reaction chamber.

20. The computer-implemented method of claim 5, wherein the automated chemical synthesis equipment includes a chemical reaction chamber where the target molecule is synthesized via a chemical reaction, the method further comprising:
    removing, by the processor using the automated chemical synthesis equipment, an aliquot of material from chemical reaction;
    determining, by the processor using the synthetic pathway engine and the automated chemical synthesis equipment, whether the aliquot satisfies one or more user-criteria for the target molecule; and
    adjusting, by the processor using the synthetic pathway engine and in response to determining that the aliquot does not satisfy the one or more criteria for the target molecule, the synthesis of the target molecule.

* * * * *